(12) United States Patent
Bonfiglio et al.

(10) Patent No.: US 7,835,498 B2
(45) Date of Patent: Nov. 16, 2010

(54) AUTOMATIC CONTROL OF A MEDICAL DEVICE

(75) Inventors: Silvio Bonfiglio, Saronno (IT); Joost Kramer, Eindhoven (NL); Franco Martegani, Mozzate (IT); Manuel Fernandez Guerrero, Malaga (ES)

(73) Assignee: Koninklijke Philips Electronics N. V., Eindhoven (NL)

( * ) Notice: Subject to any disclaimer, the term of this patent is extended or adjusted under 35 U.S.C. 154(b) by 311 days.

(21) Appl. No.: 11/815,866

(22) PCT Filed: Feb. 17, 2006

(86) PCT No.: PCT/IB2006/050535

§ 371 (c)(1),
(2), (4) Date: Aug. 9, 2007

(87) PCT Pub. No.: WO2006/087689

PCT Pub. Date: Aug. 24, 2006

(65) Prior Publication Data

US 2008/0253519 A1    Oct. 16, 2008

(30) Foreign Application Priority Data

Feb. 18, 2005    (ES)    ............................ 200500366
Feb. 18, 2005    (ES)    ............................ 200500367

(51) Int. Cl.
*H05G 1/30*    (2006.01)
(52) U.S. Cl. ...................................... 378/115; 378/205
(58) Field of Classification Search ........................ None
See application file for complete search history.

(56) References Cited

U.S. PATENT DOCUMENTS

| | | | |
|---|---|---|---|
| 5,091,926 A | 2/1992 | Horton et al. | |
| 5,558,619 A | 9/1996 | Kami et al. | |
| 5,850,211 A | 12/1998 | Tognazzini | |
| 5,886,683 A | 3/1999 | Tognazzini et al. | |
| 5,911,036 A | 6/1999 | Wright et al. | |
| 5,926,264 A | 7/1999 | Beale et al. | |
| 6,175,610 B1 * | 1/2001 | Peter ............................ | 378/8 |
| 6,886,137 B2 | 4/2005 | Peck et al. | |

(Continued)

FOREIGN PATENT DOCUMENTS

DE    9218321 U1    12/1993

(Continued)

OTHER PUBLICATIONS

Brown, LM et al; "Comparative Study of Coarse Head Pose Estimation", Motion and Video Computing, IEEE, pp. 125-130, 2002, XP010628791.

(Continued)

*Primary Examiner*—Hoon Song (57) ABSTRACT

System and method for automatic control of processes or application, such as the activation or deactivation of a radiation source for medical purposes. The system comprises an operator tracking system arranged to determine the gesture/posture of a user, an evaluation device arranged to evaluate the determined gesture/posture, and an enabling device arranged to enable and disable the radiation source in response to an output of the evaluation device. The operator tracking system may use a gazing direction analysis that may be based on the output of an eye tracking system, or an emitter-receiver arrangement for a directed signal.

15 Claims, 7 Drawing Sheets

U.S. PATENT DOCUMENTS

| | | | |
|---|---|---|---|
| 2002/0068862 A1 | 6/2002 | Kleiman et al. | |
| 2004/0212712 A1 | 10/2004 | Stavely et al. | |
| 2004/0242988 A1* | 12/2004 | Niwa et al. | 600/407 |

FOREIGN PATENT DOCUMENTS

| | | |
|---|---|---|
| DE | 9218321 | 1/1994 |
| DE | 29619277 | 2/1997 |
| DE | 29619277 U1 | 2/1997 |
| WO | 2004052225 A2 | 6/2004 |
| WO | WO2004052225 | 6/2004 |
| WO | 2005010739 A1 | 2/2005 |
| WO | WO2005010739 | 2/2005 |

OTHER PUBLICATIONS

Frigola M, et al; "Interactive Real Time Reprogramming", World Automation Congress, IEEE, pp. 425-434, 2004, XP010808319.

Frigola, et al, "Interactive Real Time Reprogramming of Surgical Robotic Taks Operating in Changing Conditions", XP10828319, pp. 1-10.

Brown et al, "Comparative Study of Coarse Head Pose Estimation", XP10628791, pp. 1-6.

* cited by examiner

AUTOMATIC CONTROL OF A MEDICAL DEVICE

CROSS REFERENCE TO RELATED CASES

Applicants claim the benefit of PCT International Application No. IB2006/050535, filed Feb. 17, 2006.

FIELD OF THE INVENTION

The present invention relates to a system and method for automatic activation and deactivation of a radiation source for medical purposes. The present invention also relates to a system and method for automatic activation and deactivation of ionising radiation controlled by the gesture and/or posture of the operator. Furthermore, the present invention relates to a system and method for automatic control by gazing of processes or applications which require visual attention or monitoring.

BACKGROUND

At present in radiological medical explorations which involve interventions, for example haemodynamic, vascular, cardiovascular, digestive, CAT, traumatology or radiotherapy interventions, etc., in order to activate the ionising radiation command (for example: x-rays, fluoroscopy, etc) and to see the image of the patient on the display monitor, it is necessary to press one or more pedals (or one switch or more switches) which are habitually located on the floor beneath the operating table, which in turn may be covered by sheets, plastic, etc., which cover the patient and the table, thus impeding the view beneath the table. Consequently, each time the operator raises his foot from the pedal in order to deactivate the ionising radiation and subsequently presses down on the pedal again (a process which occurs numerous times during the course of an intervention), it is necessary for him to look, or grope with his foot, under the table in order to locate the pedal which needs to be pressed, since there may be several pedals with different functions. This therefore wastes time before the pressing takes place, and also just after the operator has pressed the pedal, whilst he is turning his head to look at the monitor, except that in this last case ionising radiation is being produced.

Another example which occurs in practice is that during an intervention the operator looks away (for a few seconds) repeatedly, without lifting his foot from the pedal.

On other occasions, the activation pedal is pressed accidentally, with the consequent generation of radiation which is not required.

The sum of all these periods of time wasted before pressing the pedal prolongs the intervention unnecessarily, and the total of all the periods after pressing takes place, in which there is a live image (of x-rays for example), but when the operator is not looking at the monitor, means that there is an increase to a greater or lesser extent in the cumulative dose of ionising radiation received by both the patient and the staff who are in the exploration room.

This type of intervention requires continual and repeated use of ionising radiation, and its complexity may require implementation of various tasks simultaneously, such as: handling of complex instruments, the intervention itself on the patient, monitoring the vital signs, activation of ionising radiation, and observation of the images obtained on the display monitor, as well as the concentration required for any intervention work. Because of the aforementioned complexity of the work, good synchronisation of activation and deactivation of the ionising radiation is not obtained, which on some occasions gives rise to lack of deactivation of the said ionising radiation when the operator looks away from the display monitor in order to keep intervening on the patient. This means that the ionising radiation is kept active for an undesired period of time, thus increasing the dose accumulated by the patient and by all the staff who are in the exploration room.

In addition, also occasionally, the ionising radiation is activated too soon, without this being noticed.

Similar problems are caused by radiotherapy treatments: although in this case it is not necessary, the image provided by the radiation may also be displayed. However, the purpose of this therapy is to destroy the tumoral tissues. This therapy is effective only if the patient is immobile in the position on which the radiation is focussed, since otherwise all that happens is that the patient is irradiated unnecessarily. It therefore appears logical to emit radiation only after the operator has checked on a monitor that the patient is in the correct position and is not moving, and whilst he is focussing his attention on the corresponding controls or indicators which are situated in a predetermined direction.

Similarly, outside the medical domain, certain processes or applications exist, which, as they are carried out, require visual attention or monitoring, which can be implemented by means of a monitor, by means of some indicators, or directly.

For example, there is the simple activity of watching the television. On many occasions the television set is left switched on without anyone paying attention to it.

Another example consists of observing by means of television with multiple cameras and monitors. If the observer is looking at a single monitor, the other monitors and their corresponding cameras are switched on and are consuming energy unnecessarily.

There are also computer screens which are left switched on for many hours unnecessarily. Despite having automatic timed disconnections for energy saving, they lack a system which activates them simply by the fact of looking at them, thus requiring manual action on the keyboard or mouse, which is sometimes a complicated matter, for example if someone is talking on the telephone and writing at the same time.

There is also the unnecessary waste of energy, which would be eliminated by use of the system according to the invention.

However, it is not only in the context of energy saving with reference to the connection or disconnection of a monitor that control by gazing is relevant. Other possible applications also exist.

For example, in certain industrial processes it is necessary to have detailed monitoring on a screen, by means of indicators, or directly, in order to prevent industrial work (for example welding or tooling) from being carried out defectively. Thus, this work should not be allowed to be carried out if this monitoring is not being carried out by the operator.

The invention can also be applied to other fields, in order to activate various processes wherein, because of the complexity of the work and/or because it is not possible to use one's hands, various activations or processes can be executed by gazing at one or more points of reference in order to activate, deactivate and/or control them.

Similarly, the control of activations of multiple processes can be simplified to a single control, and it is possible to select the activation process required by gazing at the different points of reference. For example, several barriers to be opened up can be controlled by a single control unit, since the process would be selected by the gesture of looking at the corresponding points of reference or monitors.

In the above-described examples, control by gazing does not exist. The system and method according to the invention enhance existing systems, devices, and methods.

SUMMARY OF THE INVENTION

The purpose of the system according to one embodiment of the present invention is to increase the safety and convenience of use whilst reducing the aforementioned cumulative dose of e.g. ionising radiation.

According to the invention, a system for automatic activation and deactivation of a radiation source for medical purposes comprises an operator tracking system arranged to determine the posture and/or gesture of a user, an evaluation device arranged to evaluate the determined gesture, and a control device arranged to control the radiation source in response to an output of the evaluation device.

A related method for automatic activating and deactivating of a radiation source for medical purposes comprises the steps of
  determining the posture and/or gesture of a user;
  evaluating the determined posture and/or gesture; and
  controlling the radiation source in response to a result of the step of evaluating.

A radiation source that may be activated or deactivated emits a certain amount of radiation while it is activated. While the radiation source is deactivated, the amount of radiation is significantly lower. The terms activating, deactivating, and controlling may also comprise activating a certain mode of operation of the radiation source, such as the mode of operation that is used to produce a given amount of radiation. Activation and deactivation may be achieved by applying and suppressing a supply voltage to the radiation source. Alternatively, the radiation source may be covered by a lid or screen. An operator tracking system determines posture and/or gesture of the operator, for example which direction the operator is facing, where the operator is looking, if he is standing upright, arm or hand gestures etc. An Evaluation device determines, whether the determined posture and/or gesture of the user coincides with a predetermined gesture and/or posture signifying a specific function that the operator wants to execute. For example, the direction the user faces could be used to determine whether the operator watches an observation region, which means that the user watches information displayed and/or events occurring in the observation region. An Enabling device converts the result determined by the evaluation device to a physical interaction, such as interrupting the power supply or parts thereof to the radiation source, or instructing the radiation source to switch over into a non-emitting or low-emitting mode. To this end, the enabling device may be operatively connectable or connected to the evaluation means.

According to the invention, the system is of the type which comprises an emitter element for ionising radiation as the radiation source. The ionising radiation may pass through part of the anatomy of a patient in order to obtain images for radiology. The element emits ionising radiation (x-rays, fluoroscopy, radiotherapy, etc), which can be picked up by an element which is sensitive to the radiation after it has passed through the anatomy of the patient, who is interposed between the emitter element and the said sensitive element, for example on an operating table or stretcher.

The system may also comprise a display monitor, whether the image is picked up by the sensitive element or is an external image of the patient picked up by a video camera. The emission or cut-off of the radiation is usually controlled by a switch or pedal operated by the operator.

The improvement which an embodiment of the invention proposes consists of incorporating, as the operator tracking system, a device for control by gaze detection in the control unit for activation or emission of the radiation. This device detects whether the operator, who is usually a doctor, is looking or not at the monitor which displays the images obtained, or whether he is looking in another predetermined direction where the controls or indicators which require his attention during the irradiation are located. If this is the case, it permits or directly gives rise to the emission of the radiation, and optionally cuts it off or inhibits it otherwise.

Associated with this device and with the pedal or switch there may be also implemented an operating mode selector, since, depending on the interventions concerned, it may be contemplated to have combined functioning of the control by looking and using the pedal or switch, or control independently by means of one or the other. In addition, the device also optionally incorporates acoustic and/or optical indicators which permit or assist the precision and calibration of the device for control by viewing, and detection of whether emissions of radiation are being produced, if the operator is not looking at the monitor or the corresponding indicators and controls.

This therefore addresses the following issues:
  Reduction of the dose of ionising radiation received by the patient and by the remainder of the staff who are in the exploration room, as a result of improved control of the method for activation of the ionising radiation.
  Impossibility of the occurrence of premature activation of the ionising radiation, before the monitor is observed or before the operator is looking in the predetermined direction where the controls and indicators are located.
  Inhibition of emissions of radiation by the pedal being pressed accidentally, as well as of subsequent accidental activation of other synchronised devices. By way of example, one of these devices can be a contrast injector pump.
  Increase in the handling comfort in the process of repetitive activation-deactivation, which takes place during medical radiological intervention explorations.
  Improved precision, since it is not necessary for the operator to keeping pressing his foot down on the activation pedal and raising it continually, because these repetitive actions make the operator change his position on the floor, and this involves a slight imbalance which is reflected in reduction of the precision in the process of these interventions.
  Increased safety in activation of the process, since in addition to the original activation system itself, there is the condition of observation of this process, which is implicit in the system which is the subject of the present invention, for activation-deactivation by means of the gaze of the operator.

In an embodiment, the operator tracking system (such as a device for control by gaze detection) takes the form of a detector of the silhouette of the operator which is based on detectors of position or movement, and of processing by software. Silhouette detection is a robust method for deriving the gazing direction of a user. Even under poor lighting conditions and with the user wearing glasses or contact lenses, silhouette detection provides reliable results. The accuracy of silhouette detection can be improved by carrying out a calibration prior to using it.

The position and/or movement detectors may consist of one or more video cameras, whereas the software processes by seeking in the images obtained the position of a point of reference which is usually situated in the space between the eyebrows of the operator, or identification of the symmetry of his silhouette. For example, the one or more video cameras act as silhouette tracking system, while the software acts as the evaluation means.

The device for control by gaze detection may take the form of an element which emits a directed signal which is received by an element to receive the signal when the head of the operator doctor is positioned such that he is looking in the predetermined direction. The underlying principle may be understood like that of a beacon. At least one of the emitting element and/or the receiving element has a relatively narrow lobe. The opening angle of the lobe defines the accuracy of the gaze detection.

The emitter element may be attached to the head of the operator, whereas the receiver element is positioned in a fixed location. The receiver element detects, when it receives a signal from the transmitter, indicating that the user is looking in the direction of the receiver element. The receiver element issues a corresponding signal. The receiver element being positioned in a fixed location, the signal issued by the receiver element can be transferred to a downstream processing unit without the need for wireless transmission techniques.

Both the emitter element and the receiver may be positioned in locations such that the directed signal emitted by the emitter is detected by the detector when it is reflected on one or more portions of reflective material secured to the head of the operator, when he positions his head such that he is looking in the predetermined direction. In order for the reflection to correspond to the gazing direction, the reflective material is fixed in a certain manner. In particular, it is taken care of that the perpendicular of the reflective material (e.g. a mirror) is substantially parallel to the gazing direction of the user. This may be achieved by using a fixation for fixing the reflective material to the head of the user which can be mounted in a single manner, thus ensuring the proper orientation of the reflective material. For example, the nose of the user may be used as a point of reference for defining the gazing direction.

According to another embodiment, the emitter element, receiver, or reflector attached to the head of the operator, is implanted in goggles. Due to the direct relation between the gaze direction and goggles, the emitter element, receiver, or reflector assume a well defined orientation with respect to the eyes of the user and accordingly his primordial gazing direction.

The emitter element, receiver, or reflector attached to the head of the operator, may be disposed on an adjustable support on the face or forehead of the operator. This arrangement offers increased flexibility for the fine tuning of the gaze detection.

There are as many detector and/or emitter elements as necessary, which are for example directed such as to cover all the positions of work of the operator doctor. This assures a large field of view of the gaze detection system.

The receiver of the directed signal may include a signal which permits passage only of the signal obtained from the emitter. This filters out any other signals so that the reliability transmission is improved.

The operating mode selector may comprise at least four operating modes, i.e. one of maximum safety which requires pressing of the pedal or button and directing of the gaze in the direction predetermined for the emission of radiation; another, fully automatic mode which requires only directing of the gaze in the direction predetermined for the emission of radiation; another, deactivation mode which requires only pressing of the button or pedal for the emission of radiation; and another mode according to which the gaze in the predetermined direction activates the emission of radiation, which continues until it is disconnected by means of the pedal or switch, or automatically if the gaze does not return to the predetermined direction at regular intervals established. This offers a high degree of flexibility to the user. According to his preferences or needs, the user may set the operating mode.

The operating mode selector may be used manually so that the user may use it in an accustomed manner.

The operating mode selector may be operated by means of combinations of pressing operations carried out on the pedal. If the user cannot use his hands during an interventional procedure or surgery, he may nevertheless switch the system to another operating mode using his feet.

The mode selector may comprise certain acoustic and/or optical indicators which are associated with certain operating modes which are used for spatial orientation and/or calibration, in one of which the indicators are made to function when the operator is looking in the predetermined direction, and in the other of which the indicators function when radiation is emitted without the operator looking in the predetermined direction. This functionality offers valuable feedback about the operation of the radiation source to the user. It may assist the user in reducing the radiation dose as much as possible.

The system controls indirectly other devices which are synchronised with the emission of the radiation, such as a contrast injector, lighting of the room, control of the video, and display of images, etc. This avoids unnecessary operation of periphery. In the case of contrast agent or the like, the dose administered to the patient is reduced.

The device for control by gaze detection optionally includes an adjustable timer to delay the disconnection of the radiation emitter element when the operator looks away from the predetermined direction. This prevents the system from switching on and off too quickly.

The signal which is emitted by the signal emitter incorporates coding which can be identified by the rest of the system, in order to distinguish it from others, and to permit work by various (doctor) operators jointly and simultaneously in different activations, without interference between them. This also helps to block out disturbing signals.

The system can additionally be implemented for the voice command system. The voice command system may take the place of e.g. the pedal. The doctor may speak certain commands and the system responds to those commands by switching to another operating mode, for example.

The directed signal is of an infrared nature. Infrared light being not visible, it will not disturb the user in his task. Furthermore, infrared light can be bundled to a narrow lobe, which defines the accuracy that can be achieved.

The directed signal is of an ultrasonic nature. Ultrasonic sound being not audible, it will not disturb the user in performing his task. Furthermore, ultrasonic sound waves can be bundled to a narrow lobe, which defines the accuracy that can be achieved.

According to another embodiment, the system according to the invention acts in an optimum manner in order to carry out automatic control of any process or application which involves an electric control unit, and or which requires visual attention or supervision.

The control which is carried out by the system consists of switching (connection or disconnection by means of the electric control unit) of the process or application when there is detection of the gesture carried out by the observer when he looks at a point of reference, i.e. when he positions his head such that his gaze faces this point, or when he does not look at this point. This point of reference can be for example a monitor, which physically displays the part of the process to be monitored, some indicators which show the value of some parameters to be monitored, or the location where the process is taking place.

For this purpose, the invention comprises the implementation of an emitter of a directed signal of a suitable nature, for example an infrared or ultrasonic signal, which is designed to be picked up by an appropriate detector, i.e. of the same nature as the emitter. If considered appropriate, and especially in surroundings where there may be other signals with a similar nature, the signal can include particular coding which differentiates it from the other signals.

For a similar purpose, a method for automatic control by gazing of processes or applications which require visual attention or monitoring, only when monitoring is being carried out, comprises the steps:

Emitting a directed signal of a suitable nature from an emitter;

Picking up the directed signal by a suitable receiver;

Determining the orientation of the head of the observer of the system;

Determining, whether the observer's eyes face a point of reference;

Driving control electronics which form part of an electric control unit which is associated with the receiver and which controls the activation or deactivation of the application or process.

The spatial arrangement of the emitter and receiver will be such that the signal will be received by the receiver only when the head of the observer is facing the point of reference, such that, by means of associated electronics which act as an electric control unit for the process or application, the latter will be activated in this case. Similarly, if the head of the observer is not facing the point of reference, the process will be paused or deactivated.

Since the head is the part of the anatomy of which the orientation is to be detected, there must be secured to the head one of the aforementioned elements, i.e. the emitter or receiver, or an element which can reflect the signal to the receiver.

The point of reference is located in a monitor which displays the process. Accordingly, the user automatically validates a command for activating the function only, if he is looking at the monitor. It should be noted that the point of reference does not have to coincide with the emitter, receiver or reflective element. The system can be calibrated so that e.g. the emitter is situated on top of the monitor, while the point of reference is situated in the middle of the screen of the monitor.

The point of reference is located in some indicators which show parameters of the process. Accordingly, the user automatically validates a command for activating the function only, if he is looking at the indicators.

The point of reference is situated directly in the location of the process. Accordingly, the user automatically validates a command for activating the function only, if he is looking at the process.

The directed signal is of an infrared nature. Infrared light being not visible, it will not disturb the user in his task. Furthermore, infrared light can be bundled to a narrow lobe, which defines the accuracy that can be achieved.

The directed signal is of an ultrasonic nature. Ultrasonic sound being not audible, it will not disturb the user in performing his task. Furthermore, ultrasonic sound can be bundled to a narrow lobe, which defines the accuracy that can be achieved.

In a variant embodiment of the invention, the emitter is fastened to the head of the observer, and the receiver is situated in a fixed location. Accordingly, the receiver can be connected to further processing means, such as an evaluator for the gaze direction.

In a variant embodiment of the invention, the receiver is fastened to the head of the observer, whereas the emitter is situated in a fixed location. In this case, the receiver, e.g. via a radio link or an infrared link, sends a signal back to the receiver, which forwards it to further processing means, such as an evaluator for the gaze direction.

Alternatively, both the emitter and the receiver are fastened to the head of the observer, whereas an element which reflects the signal is situated in a fixed location.

Another alternative is that both the emitter and the receiver are situated in fixed locations, whereas at least one element which reflects the signal is fastened to the head of the observer. Having both, emitter and receiver in fixed locations allows that they may be connected by means of cables or the like. Neither emitter nor receiver needs to be battery powered. The reflective element is comfortable to wear, because it is light weight and does not heat up during use.

According to another embodiment, the emitter element, receiver, or reflector attached to the head of the operator, is implanted in goggles. Due to the direct relation between the gaze direction and goggles, the emitter element, receiver, or reflector assume a well defined orientation with respect to the eyes of the user and accordingly his gaze.

The emitter element, receiver, or reflector attached to the head of the operator, may be disposed on an adjustable support on the face or forehead of the operator. This arrangement offers increased flexibility for the fine tuning of the gaze detection.

The signal can optionally be provided with coding in order to distinguish it in an environment where there are signals of a similar nature, corresponding to implementation in the receiver and/or control electronics of the possibility of identifying the said coded signal. This helps to block out disturbing signals.

The receiver can optionally be provided with a filter in order to distinguish other signals with a different wave length from that of the signal emitter by the emitter. This helps to block out disturbing signals.

According to another embodiment of the invention, a system for automatic controlling at least one function of at least one medical device is proposed. The system comprises an operator tracking system arranged to determine the posture of an operator of the medical device, an evaluation device arranged to determine whether the determined posture indicates that the operator exploits said function of said medical device, and an control device arranged to control the function of the medical device.

According to a related embodiment, a method for automatic control of at least one function of at least one medical device comprises the steps of:

Determining by means of an operator tracking system the posture of an operator of the medical device;

Determining by means of an evaluation device, whether the determined posture indicates that the operator exploits said function of said medical device; and Controlling said function of the medical device by means of a control device.

A function of a medical device may be switching on or off, activating, deactivating, enabling, disabling the medical device as a whole or only partially. A function of the medical device may also be understood as a changing the mode of operation of the medical device or of parameters thereof. Control of a function of a medical device comprises causing the function to be executed. Exploitation of such a function of the medical device comprises the operator requesting the function or appreciating the result of the function, such as looking at data or information provided by the function. The ascertainment of the exploitation of a function may not always be possible with absolute accuracy. In these cases, a certain calculated confidence about the operator exploiting the function may be used. Among others, the posture of the operator may comprise where the operator is standing, which direction his body or certain body parts are aiming at, flexion of his body and/or joints, and the like. The control device converts the result of the evaluation device which indicates whether the operator exploits the function. This also comprises those cases, in which the operator requests the execution of a function. A unique gesture may be defined as a command for a certain function. In a plurality of predefined gestures, each gesture corresponds to a certain function (note that multiple assignments are also possible, i.e. there are several gestures for one function, for example one for right-handed people, another for left-handed people). If the operator performs a gesture that the evaluation device recognizes as a gesture associated with a function (e.g. "right hand with palm facing upward moves up approx. 10 cm"), then it tries to execute that function (e.g. "increase zoom of displayed image") by instructing the control device accordingly.

The evaluation device may be further arranged to determine whether the posture of the operator indicates that the operator observes a predetermined observation region. This may be achieved by evaluating for example the head position and orientation. The position and orientation of the head provides a good estimation of the actual gazing direction of the user.

The medical device may be a diagnostic device using x-rays to provide live video images which are then displayed on the screen of a monitor. Instead of x-rays, other types of radiation or waves may be contemplated, such as ultrasound, laser, electromagnetic waves in general, or the like. The invention may be used for example in the following modalities: magnetic resonance, nuclear magnetic resonance, computer tomography, positron emission tomography, echocardiography, angiography, etc. The medical device may also be a therapeutic device. The mentioned function of the medical device may be the power supply to a particular element of the medical device, but is not restricted thereto. For example, it may be contemplated to control the intensity, wavelength of radiation that is emitted by a radiation source of the medical device. This feature may be used, if the operator wishes a more detailed view of a certain anatomy. The operator tracking system may evaluate the position and orientation of the face, the head, the upper body, or the entire body of the operator.

In a related embodiment, the evaluation device is further arranged to determine whether the posture of the operator indicates that the operator observes a predetermined observation region. This may be achieved by determining whether the operator is facing the observation region, for example by analyzing the symmetry of an image of the operator captured by an appropriate image acquisition device. It may also be achieved by looking for certain features of the operator, for example his facial features.

In a related embodiment, the medical device is a radiation emitting medical device. By using the invention with a radiation emitting medical device, the radiation that a patient and/or the staff are exposed to is reduced. This reduction of radiation exposure may be achieved e.g. by (partially) interrupting or diminishing the power supply to a radiation producing element of the medical device, such as an x-ray tube. In this case the function that is paused by the system according to the invention is the power supply function of the radiation producing element. It is mentioned that a laser emitting medical device (therapeutic or diagnostic) is a radiation emitting device, as well.

The observation region may be located in a monitor displaying data relating to the medical device. Alternatively, the observation region may be located at the target site of the medical device. This links the pausing and resuming of the function of the medical device to the operator watching the monitor or the target site, respectively. Target site of the medical device means the site where the medical device interacts with the patient. For a diagnostic device the target site may be understood as the scanned volume of the patient, for a therapeutic device it may be the site of treatment.

The observation region may comprise a plurality of sub regions, each sub region being associated with the control of a specific function of the at least one medical device. This can be used in procedures, where various functions have to be controlled (multi-controls procedures). Each control is activated through data or images located on a given zone of the display's screen. In this case the probability of activating a wrong control can be minimized by conditioning the activation to the detection by the eye tracking system of the specific zone of the screen the operator addresses with his eyes.

In an embodiment, the system may further comprise an operator command input device and a signal combination device arranged to combine the respective output signals of the evaluation means and the operator command input device. Accordingly, the operator may command the function of the medical device to some extent. In particular, the operator may activate the function by means of the operator command input device when he is about to perform the critical step(s) of the intervention, for which live x-ray video support is required (long term activation of the function). However, the operator does not need to deactivate or pause the function (e.g. x-ray emission) while performing the critical step(s). The fact whether the operator is watching the observation region is determined by the eye tracking system and the evaluation means. If it is determined that the operator is not watching, the input to the signal combination device relating to the evaluation means assumes a value that causes the signal combination device to generate a signal which in turn causes the enabling means to pause or disable the function of the medical device. As such, the eye tracking system and its downstream components act as an override for the function of the medical device. This override assures that the function of the medical device is activated or resumed only, if the operator is watching the observation region.

The operator tracking system may be or comprise an eye tracking system. Using an eye tracking system, the user does not have to wear equipment for example on his head. The eye tracking system is capable of determining the true gazing direction, instead of merely the direction of the head, which may be different from the true gazing direction, if the eyes of the operator are inclined with respect to their normal orientation. The determination of the gazing direction may be a simple decision whether the operator is looking in a particular direction, i.e. a yes/no decision. However, a more precise determination of the gazing direction may also be employed. The eye tracking system may also detect the state of the eye lids, i.e. whether these are open or closed. The above mentioned predetermined observation region is a region where the operator observes an intervention either directly or indirectly by means of an appropriate medical device modality. The observation region may be affected by the medical device, be it that it shows a live video or that it is exposed to radiation or the like. A purpose of the evaluation device is to provide a decision about whether the operator is looking at the observation region.

The eye tracking system may be chosen from a group comprising coil systems, Dual Purkinje systems, Corneal reflection systems, pupil boundary systems, and video based systems. Nowadays, several technologies are available for eye tracking. Some of these technologies excel in spatial/temporal accuracy, while others may be more easier to use or less expensive. As an example, for a single-control application where the eye tracking system simply has to detect if the operator is looking at the screen of the display, a video-based system using a CCD camera with visible light could represent a suitable solution. In this case, the main requirements for the eye tracker are the field of view, the viewing distance, face recognition, rather than position accuracy. Better accuracy is requested in multi-control applications where the eye tracking system has to identify the specific zone of the screen observed by the user. An infrared-based eye tracking system could be employed in this case. In both cases, a large field of view of the camera allows a certain level of freedom in the movement of the operator. Moreover, the solution has to guarantee the correct operation under different environmental and usage situations (different light conditions, different layouts, different positions of the operator, tolerance for glasses and contact lenses . . . ).

According to a further embodiment of the present invention a medical device comprises a system as described above. The medical device may further comprise a radiation source and a radiation detector. The medical device may further comprise a display for images acquired by means of the medical device.

A medical device that comprises a system as described above may provide easy manipulation. The medical device makes it possible to implement control features assisting the operator, for example a surgeon, in his interventional procedure by automating one or several functions that are usually controlled by the operator. If the medical device comprises a radiation source and a radiation detector, it is possible to reduce the cumulative amount of radiation the patient is exposed to. A display for images acquired by means of the medical device may also define an observation region the operator needs to watch if he wishes a certain function to be performed by the medical device. Accordingly, the operator must acknowledge by looking the execution of this function.

BRIEF DESCRIPTION OF THE DRAWINGS

In order to complete the description which is being provided, and for the purpose of assisting better understanding of the characteristics of the invention, the present description is accompanied, as an integral part of it, by a set of drawings in which the following is represented on an illustrative and non-limiting basis:

FIG. 2 shows various possible embodiments of the device for control by gaze detection.

FIG. 5 shows a series of variants of implementation of detection of the signal which is directed and emitted by the receiver, and of recording of the signal by the detector, according to the invention.

FIG. 6 shows two variant embodiments of attachment to the head of the user, of the emitter, detector or reflector.

DESCRIPTION OF PRACTICAL EMBODIMENTS OF THE INVENTION

Figure 1:
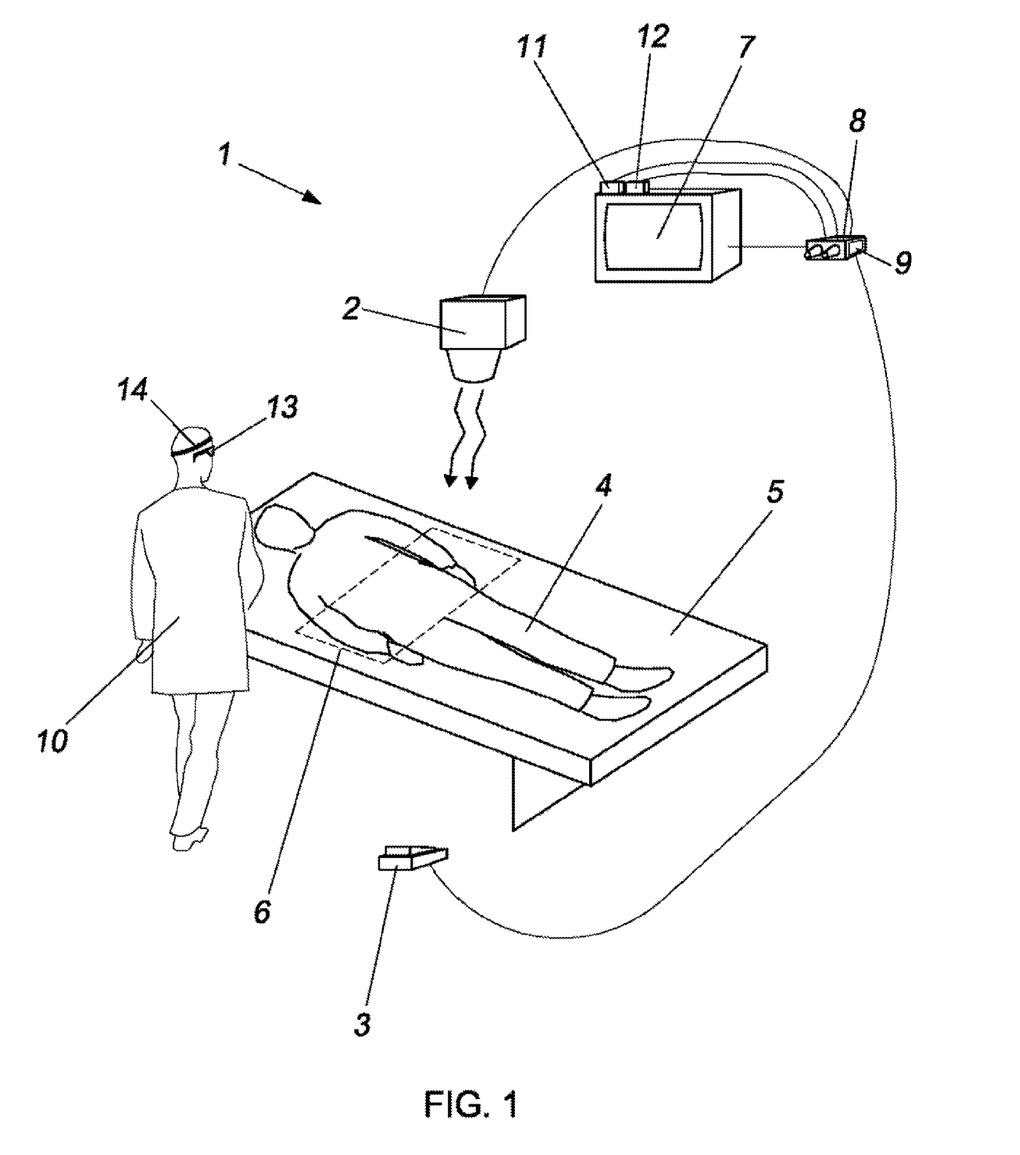
FIG. 1 is a schematic view of the system which is the subject of the present invention.

The system 1 according to the present invention consists of an element 2 which emits ionising radiation, for example x-rays, fluoroscopy or the like.

The emission of radiation by this element 2 is habitually controlled by an emission control unit which includes a pedal 3 or switch which is pressed by the operator. For as long as the pedal is pressed down, the emission of radiation takes place, and vice versa.

In the case of obtaining radiological images, the beam of radiation is directed towards the patient 4, who is usually lying on a stretcher 5, and subsequently meets an element 6 which is sensitive to this radiation. When the beam passes through the body of the patient, the absorption which occurs leads to formation of the image which is picked up by the element 6, and is transferred to the display monitor 7.

In the case of radiotherapy, the image which is shown on the screen serves the purpose only of verifying that the patient is positioned correctly, and has not moved. For this purpose, the image may be the one picked up by the element 6, or an image taken by a video camera. In this case, in addition, it may be contemplated for the gaze control unit to be focussed on the attention by means of various controls or indicators of the monitor, once the correct positioning of the patient has been checked.

The invention proposes to interpose in the emission control a device for control by gaze detection, which permits the emission of radiation only if it detects that the operator is looking at the monitor, or is focussing his attention in the predetermined direction where the controls and indicators which are needed in the case of radiotherapy are located.

In order to make the system versatile, the emission control unit includes an operating mode selector 8, which is controlled manually as can be seen in FIG. 1, or is controlled by combinations of operations of pressing the pedal. This selector can take into account at least the following modes:

Default, maximum safety mode, in which the ionising radiation is activated only when two circumstances exist simultaneously, i.e. that the operator has pressed the original activation pedal, and is looking in the predetermined direction (at the monitor or at the controls and indicators).

Safety mode applied at the beginning of activation, when the operator looks in the predetermined direction in order to activate the emission of ionising radiation, which will then continue to be applied even if he does not look in that direction, with deactivation being produced by means of the pedal or switch, or automatically if a specific interval of time elapses without the operator looking in the predetermined direction.

Fully automatic mode, in which activation occurs directly when the operator looks in the predetermined direction, without needing to press the activation pedal. Deactivation takes place automatically when he looks away from this direction.

Switched off-deactivated mode, in which the system proposed does not interfere with the normal functioning of the equipment, and consequently, in order to produce ionising radiation, only the pedal-switch is pressed.

Other modes are also possible, which can be a combination of those previously described.

It is also possible to introduce a programmable timer 9, which goes from zero to the value which is considered necessary (for example tenths of a second), in order to avoid the problems which would be caused by disconnection or interruption of the emission of radiation as a result of rapid and/or involuntary movements which presuppose that the operator is not looking at the monitor.

Since it is assumed that, by using ergonomic criteria, the simple natural gesture of the operator turning his head in the predetermined direction will activate the radiation automatically, and that in the opposite case the radiation will be disconnected, the device for control by gaze detection can be implemented by any means which achieve this purpose.

Figure 3:
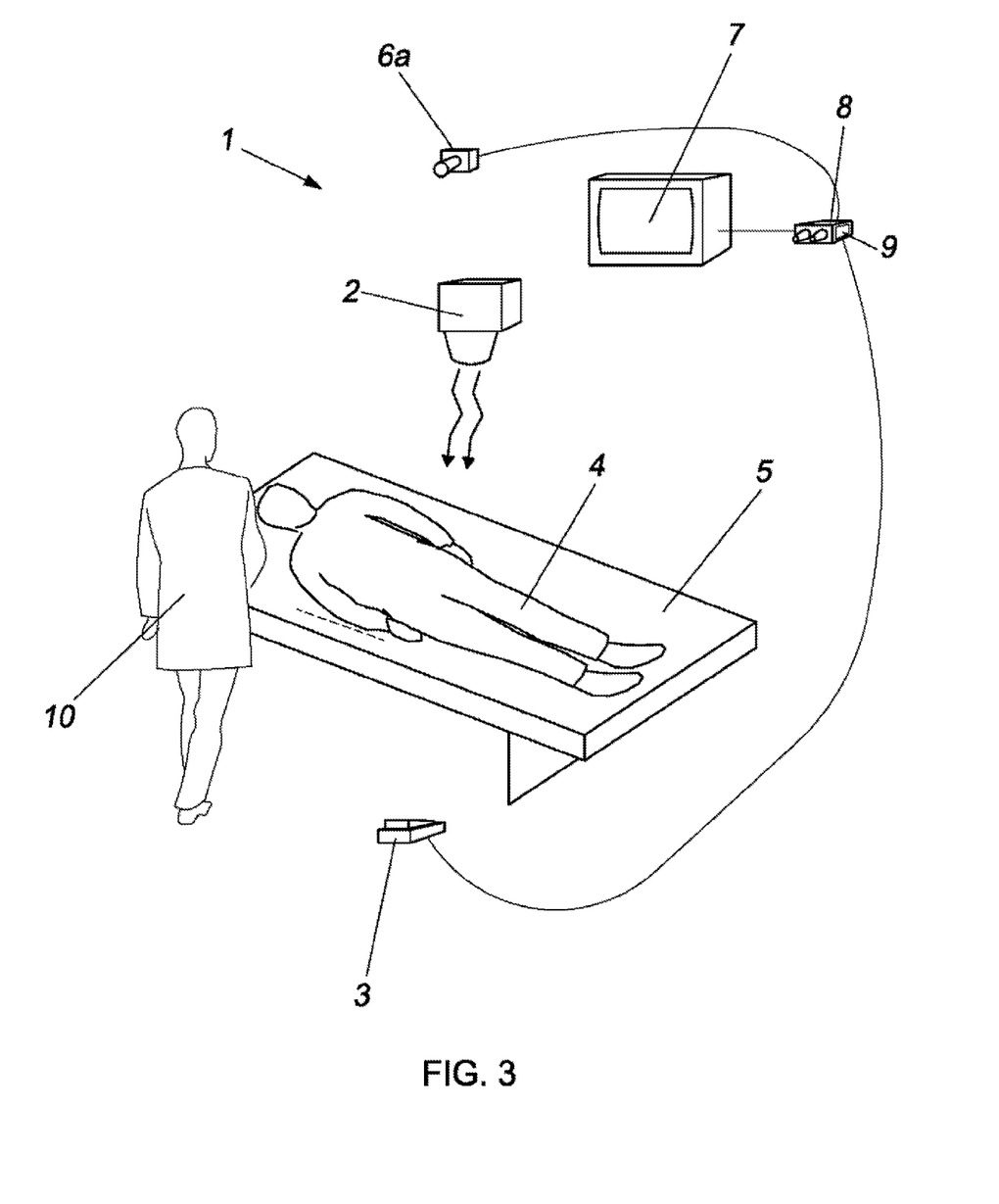
FIG. 3 shows a variant of the embodiment shown in FIG. 1, in which recognition of the silhouette of the operator is used.

By way of non-limiting example of the invention, for this device use is proposed of a unit for control or detection of the silhouette of the operator 10 by means of detectors for position and/or movement and by means of processing by software. The position and movement detectors may consist of a video camera 6a, whereas the software would monitor a reference point, for example the space between the eyebrows of the operator, or the symmetry of his silhouette, in the images obtained. It may also be contemplated to have the system observe the other body parts of the operator, such as the hands, or the entire body. When the processing identifies that the operator is looking in the predetermined direction (at the monitor or at the controls and indicators), this will give rise to emission of the ionising radiation.

Figure 23:
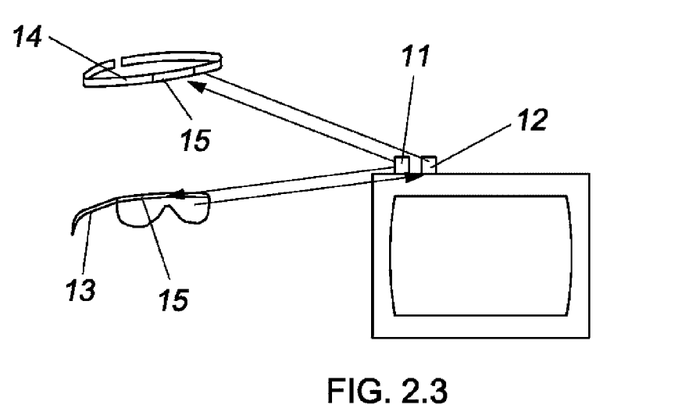

Another, simpler embodiment could consist of implementing the device by means of an element 11 which emits a directed ultrasound or infrared signal, and a receiver 12 for this signal. The positioning of these elements will be such that the signal emitted by 11 will reach the receiver 12 only when the operator is looking at the monitor or in the appropriate direction. For this purpose, the emitter can be located in the monitor, and the operator can wear the receiver, or vice versa. Also, for example, the emitter and receiver can be located in the monitor, or they can be worn by the operator, and use can be made of a reflector 15 which reflects the signal emitted and to be picked up. The most rational solution may be that shown in FIGS. 1 and 2.3, in which the emitter and receiver are placed in any suitable location, such as in the monitor, whereas the operator wears a reflector 15, for example in his goggles 13, which may or may not be leaded, or on a support 14 which is adjustable to the head, occupying the surface area necessary, and reflecting the signal which is emitted to the detector when the operator turns his head towards the monitor.

The detectors for position and/or movement could also be based on another principle, such as a position sensing system having one or more emitters attached to the user and a plurality of receivers. In this case, the signal need not be a directed signal. The determination of the position is achieved by measuring the time delay between signals received at the different receivers. By using two or more emitters, each emitting a characteristic signal, even the orientation (i.e. among others the gazing direction) of the operator may be determined, if the two emitters are attached to different parts of the body of the operator, i.e. one of the emitters is attached to e.g. the forehead and the other is attached to the back of the head.

If necessary, the receiver 12 can incorporate a filter, not shown, which will permit passage only of light with a wave length which corresponds to that of the infrared emitter, in order to prevent other emissions with other wave lengths from being able to interfere in the activation of the system. It would also be possible to implement in the directed signal coding which distinguishes it from other signals, and to provide the detector and/or the system electronics with the capacity to make the corresponding identification and discrimination.

As many emitter or receiver elements will be provided as is necessary to cover all of the area of work of the operator doctor.

Since the system controls the emission of the radiation, it will also control indirectly the functioning of other synchronised elements, such as the light in the room, video, and display of images, etc.

Voice activation commands may also be implemented in the system, in order to co-operate in the procedure with optimum convenience and minimum irradiation.

Figure 4:
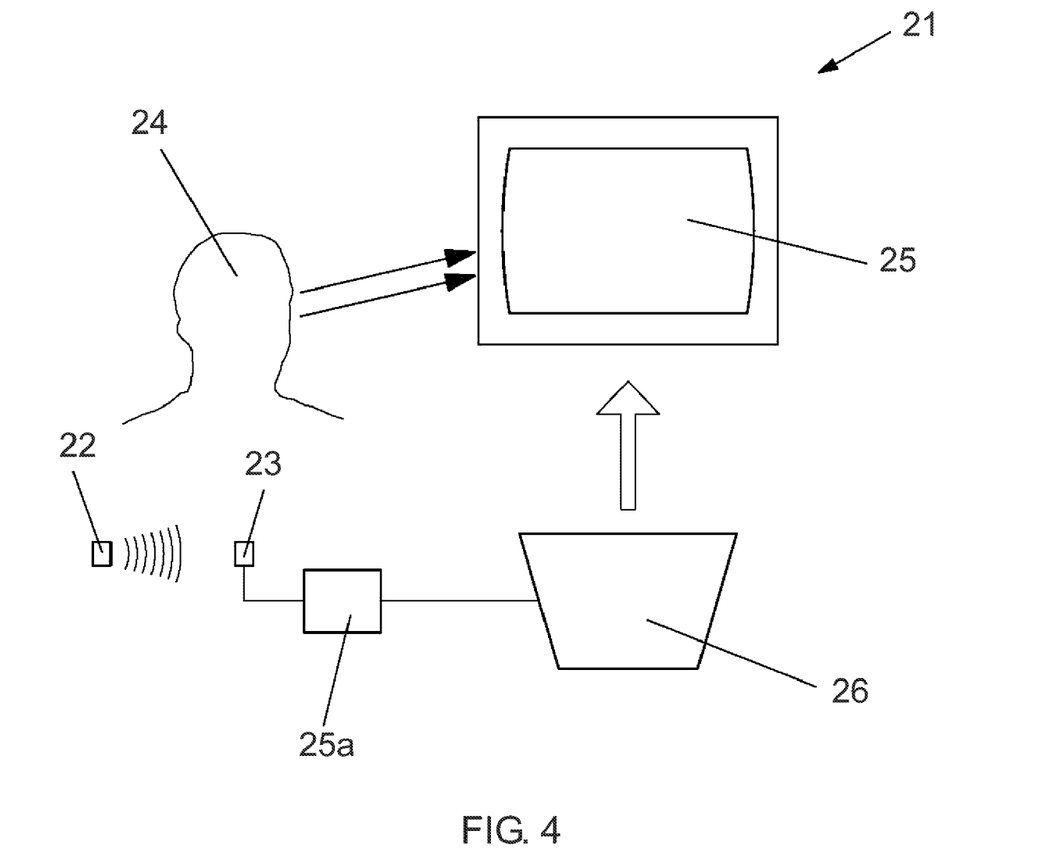
FIG. 4 shows schematically another embodiment of the system according to the invention.

In FIG. 4, the system 21 according to another embodiment of the invention comprises an emitter 22 of a signal of a suitable nature, such as a directed infrared or ultrasonic beam, which is designed to be received by a suitable receiver 23, only when the head 24 of the observer of the system is positioned such that his eyes are directed towards the point of reference, which in this non-limiting example of the invention consists of a monitor 25 which displays the process, or vital parts of it.

At such a moment, control electronics 25a for the process or application 26, associated with the receiver 23, will give rise to connection or activation of the process 26, whereas if this is not the case they will give rise to deactivation of the process.

Figure 51:
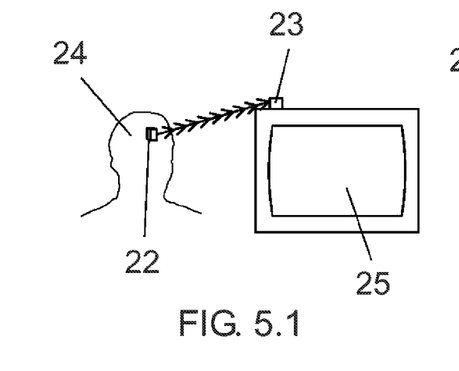

In order to obtain receipt of the signal emitted by the emitter 22 at the receiver 23 under these circumstances, the following implementations are proposed:

Fastening of the emitter 22 on the head 24 of the observer, and placing of the receiver in a fixed location, ideally on the monitor 25 itself (FIG. 5.1).

Figure 52:
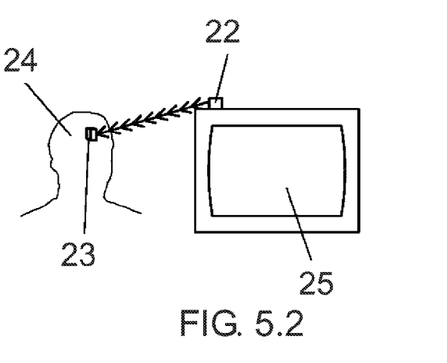

Fastening of the receiver 23 on the head of the observer, and placing of the emitter in a fixed location, ideally on the monitor 25 itself (FIG. 5.2).

Figure 53:
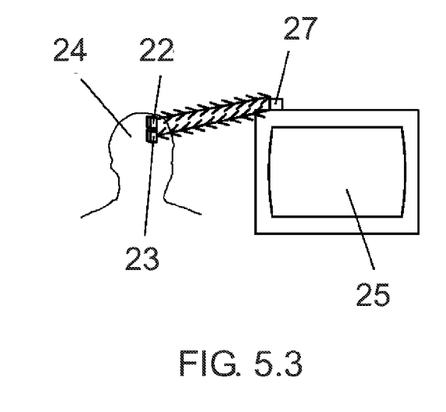

Fastening of both the emitter 22 and the receiver 23 on the head of the observer, corresponding to the positioning in a fixed location, ideally on the monitor 25 itself, of an element 27 to reflect the signal emitted by the emitter, in order for this signal to be received after being reflected back to the receiver (FIG. 5.3).

Figure 54:
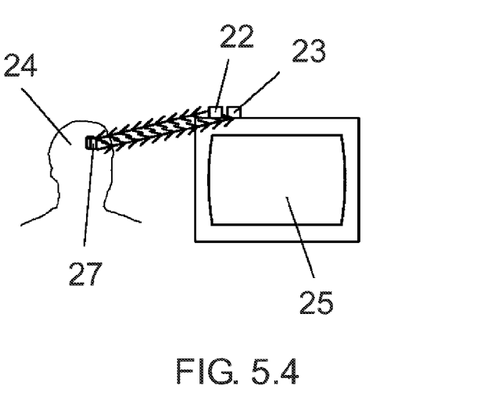

Positioning of both the emitter and receiver in the fixed location, such as on the monitor 25, corresponding to fastening onto the head of the observer of an element 27 to reflect the signal (FIG. 5.4).

With this last configuration there is no need for the observer to wear certain elements, i.e. emitters or receivers, which require sources of energy and/or connections, whether these are wireless or wired, to the control electronics 25a.

It should be taken into account that the fixed locations where the emitter, receiver or reflector described in the preceding cases is located, need not coincide with the fixed point of reference towards which the gaze is directed. They can be in any location, provided that the condition is fulfilled that the signal reaches the receiver only when the head of the observer is positioned such that his eyes are facing the point of reference.

Figure 61:
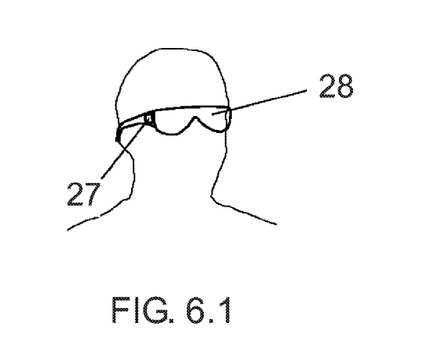
Figure 62:
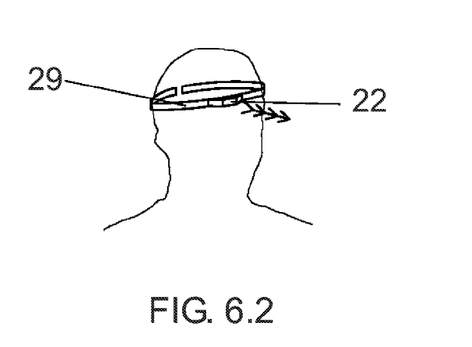

The fastening to the head of the wearer of the elements (emitter, receiver, reflectors or other emitters of communication to the control electronics) which are necessary for functioning of any of the configurations of the system, can take many forms. By way of non-limiting example, the insertion of these elements is proposed in goggles 28, or on a support or band 29 which is adjustable on the head or forehead of the observer, as represented respectively in FIGS. 6.1 and 6.2.

It will be appreciated that the positioning of the emitter 22, receiver, and if applicable the reflecting element 26, will be such that the direct or reflected incidence of the signal on the receiver will take place only when the head of the user is facing the screen of the monitor.

Optionally, if the system is installed in a location where there are signals of the same nature, the signal of the system can be provided with coding to identify it or distinguish it from others, associated with the service of detection of this identity implemented in the control electronics. Also, or optionally, the receiver can be provided with a filter, not shown, which distinguishes signals with different wave lengths.

Finally, the system can be combined with other systems for switching or manual or automatic control of the process or application, thus providing mixed control which will provide greater security of operation.

Figure 7:
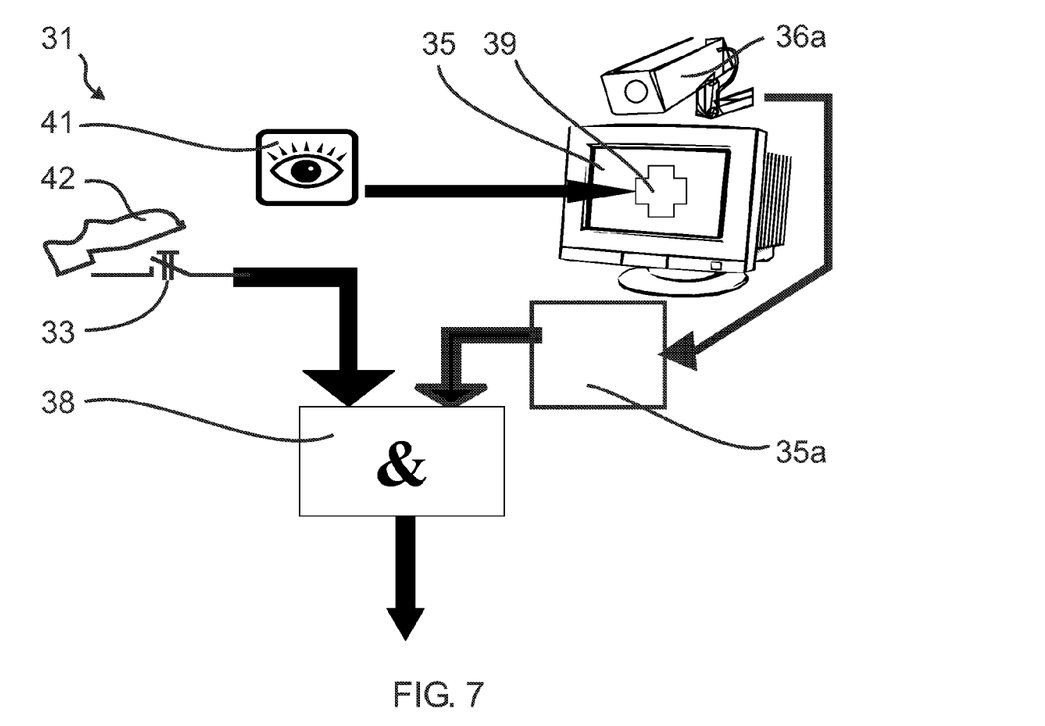
FIG. 7 is a schematic view of the system which is the subject of another embodiment of the present invention.

FIG. 7 shows a system according to a embodiment of the present invention. The system 31 may be used for automatic pausing one or several functions of a medical device (not shown). System 31 comprises a video camera 36a and an associated image analysis and evaluation entity 35a, such as a computer running an appropriate program. The camera 36a is connected to the image analysis entity 35a and mounted on top of a monitor 35. An eye tracking system is a part of the system according to the embodiment that is currently described. FIG. 7 schematically shows the eye 41 of an operator. The eye tracking system may comprise camera 36a and parts of the image analysis entity 35a. Its purpose is to determine what direction the operator of the medical device is looking at. This may also be achieved by evaluating the gesture and/or posture of an operator. Regarding the underlying technology, this functionality may be achieved by one of the following technologies: Iris recognition, silhouette recognition, or IrDA camera with Corner Cube Reflector. Other technologies for determining the gazing direction of an operator more or less accurately that do not use a camera are for example inertial tracking, position sensitive detector, sensorial EOG (electrooculogram), transmitter/receiver systems based on infrared or ultrasound, or light guns. The image analysis and evaluation entity may also comprise means to evaluate whether the operator looks at a predetermined observation region, i.e. whether his gazing direction targets the observation region. This may be necessary, if the observation region is not in the near vicinity of the camera 36a, since in these cases a straight forward binary decision as to "operator is looking/is not looking in the direction of the camera" may not work anymore. Also in those cases, in which the observation region is subdivided in a plurality of sub regions (see description of FIGS. 9 and 10 below), the gazing direction needs to be determined more precisely, for example in terms of azimuth and elevation angles, or in terms of regions such as "centre of the screen", "lower left corner of the screen" etc. In FIG. 7, monitor 35 displays a target 39, which the operator needs to look at if he wishes to resume the function of the medical device that is associated with the target. System 31 furthermore comprises a pedal 33 to be operated by a foot 42 of the operator. The output port of the pedal is connected to a signal combination device 38. Another input of the signal combination device 38 is provided by the output of the image analysis entity 35a. The signal combination means 38 combines both signals by means of a logical AND. The output of the signal combination means is valid if both input signals are valid. Thus, the behaviour is as follows: While the operator is not looking at the display (corresponding to the observation region), the eye tracking system does not validate an unintentional activation of the function of the medical device. For a cardiovascular interventional procedure, the function may be for example the fluoroscopy flow or the power supply for the x-ray tube. While the operator is watching the screen during his intervention, he activates through pedal 33 the fluoroscopy flow and the eye tracking system validates the command. The fluoroscopy flow or the power supply of the x-ray tube will resume for as long as both input signals to the signal combination means 38 are valid.

Figure 8:
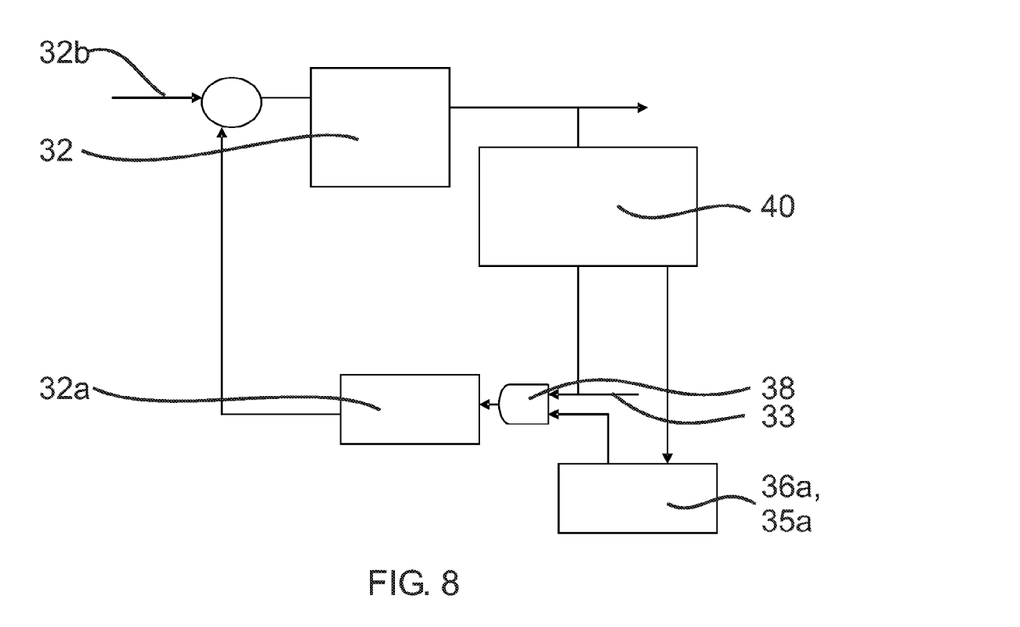
FIG. 8 is a block diagram of the system shown in FIG. 7.

FIG. 8 shows a block diagram of a part of the eye tracking system and the medical device. When performing fluoroscopy, the following conditions must be fulfilled. There is a need for a fluoroscopy flow, i.e. radiation. The fluoroscopy flow is produced in a fluoroscopy flow generating element 32a. Besides the fluoroscopy flow, the image acquisition sub system of the medical device has to be ready, as well. In FIG. 8, the state of the image acquisition subsystem is represented by signal 32b. Typically, the image acquisition sub system may be kept functioning during the entire duration of the cardiovascular interventional procedure, since it does not harm the patient and the staff. Furthermore, the equipment of the image acquisition sub system may not lend itself to repetitive switching actions due to its response time and possible damage to the equipment. The fluoroscopy flow on the other hand is typically harmful to human beings, such that the patient and the staff should not be exposed to it longer than necessary. In the case of an x-ray tube, a high voltage is supplied to the tube in order to create x-rays. Cutting off this high voltage supply causes the radiation the to cease. In the upper left corner of FIG. 8, a merge point is shown, which indicates that above mentioned conditions need to be fulfilled in order to obtain an x-ray image. If they are, then x-ray generation and image acquisition entity 32 generates live video images. The live video images are displayed to the doctor 40 on monitor 35 (FIG. 7) who makes a judgement based upon these images. When the doctor 40 is momentarily done looking at the live video images, he may avert his gaze from the monitor or lift his foot from the pedal 33. In the first case of the doctor averting his gaze from the monitor, this is detected by the eye tracking system and evaluation means 36a, 35a. The evaluation means 35a issues a corresponding signal to the signal combination means 38 indicating that the doctor is not longer watching the live video images in the monitor. A similar signal is issued by the pedal 33 in case the doctor or operator lifts his foot.

Figure 9:
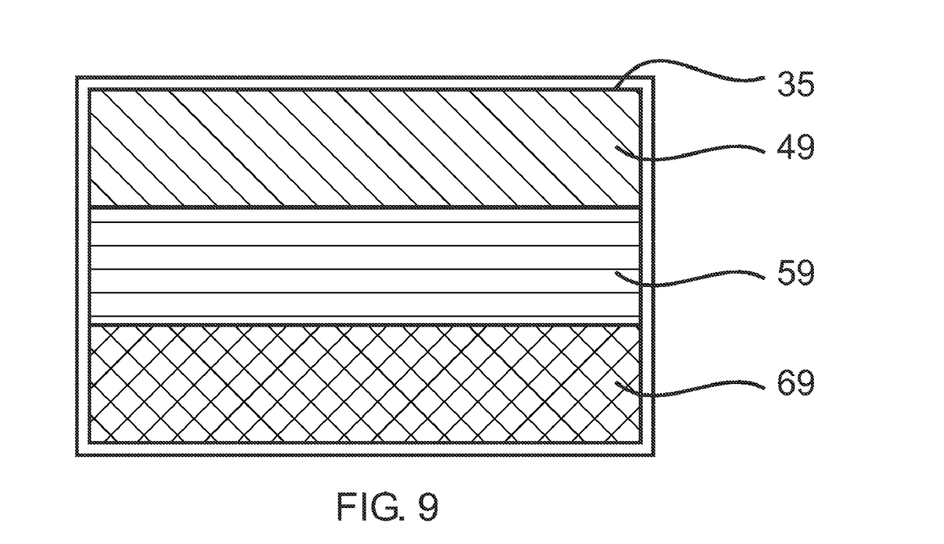
FIG. 9 shows the screen of a monitor in a related embodiment.
Figure 10:
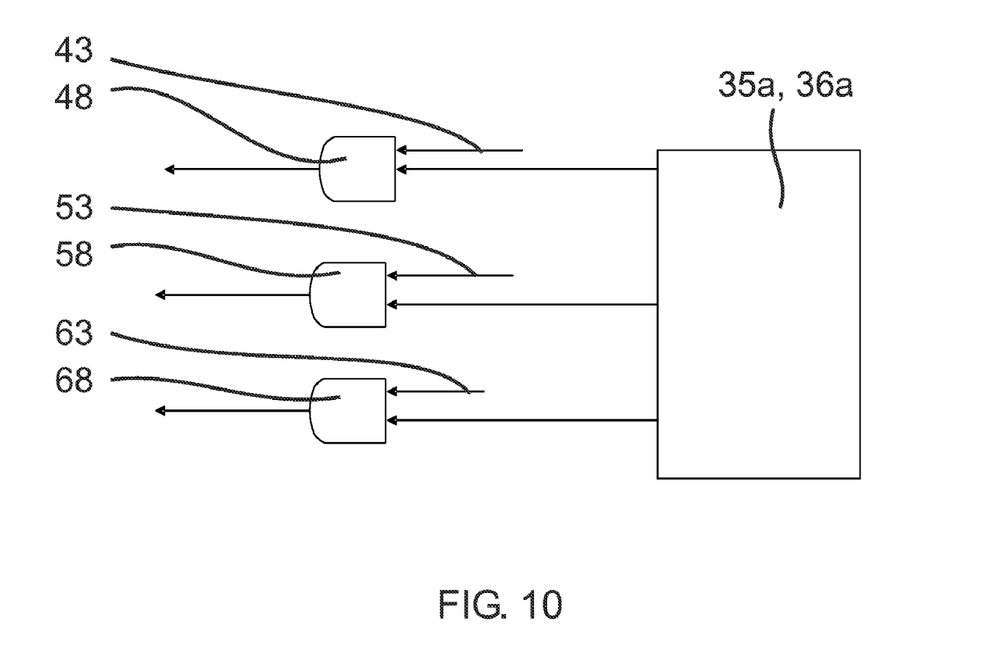
FIG. 10 shows a partial block diagram of a system that makes use of the monitor screen of FIG. 9.
Figure 21:
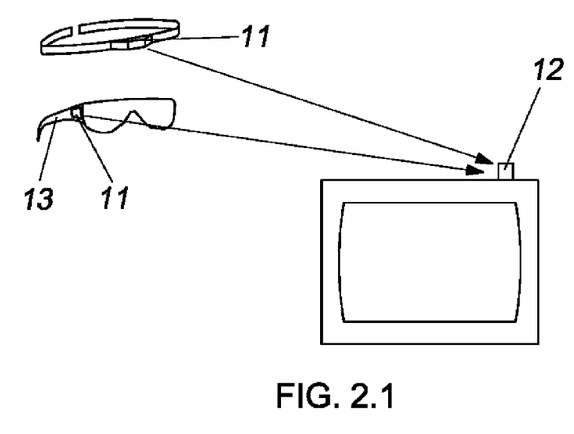
Figure 22:
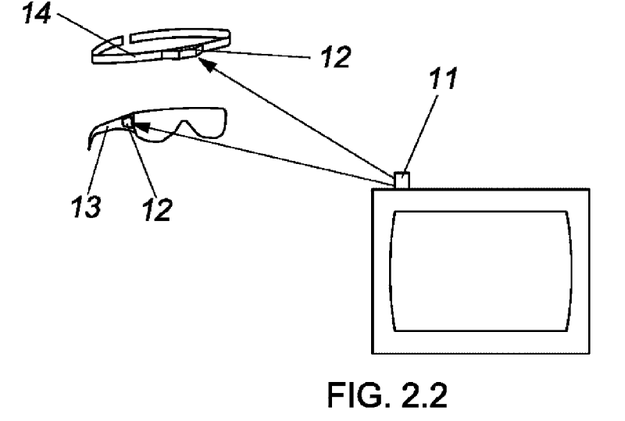

FIGS. 9 and 10 show the screen of a monitor 33 and the logic used to process information issued by the eye tracking system, respectively. The screen shows the observation area of the automatic pausing system described above. The observation area comprises three sub regions 49, 59, and 69. This approach can be used in procedures where various functions have to be controlled (multi-controls procedures). Each control 43, 53, 63 is activated depending on the status of a specific parameter which is visualized through data or images located in a given zone of the display's screen. In this case the probability of activating a wrong control can be minimized by conditioning the activation to the detection by the eye tracking system 36a, 35a of the specific zone of the screen the operator addresses with his eyes. This conditioning is performed by signal combination means 48, 59, 69 in a similar manner as performed by signal combination means 38.

A freeze image function may also be implemented in the system. The system may freeze the latest video image displayed if the operator lifts his foot from the pedal, but continues to watch the screen of the monitor. Especially in those cases in which the operator needs to carefully judge the situation before proceeding, a freeze image function may be useful. The system resumes showing live video images when the operator presses the pedal again and is watching the screen.

Another additional functionality of the eye tracking system may be the recognition of the operator from a plurality of persons watching the screen. During cardiovascular interventional procedures, not only the doctor, but also other medical staff, such as nurses may be present in the room. The eye tracking system may consider the gazing direction of the main operator (e.g. the doctor), only. This may be achieved by teaching the eye tracking system, who the main operator will be for the following procedure. During the procedure, face recognition may be used, or the operator may wear a distinctive mark, such as a patch or pin on his scrub. It may also be possible to define two or more operators. The system will then evaluate whether at least one of the operators is watching and resume, activate, or enable the corresponding function of the medical device.

Having described sufficiently the nature of the invention, and the manner of putting it into practice, it should be noted that details of the arrangements which are described above and represented in the attached drawings can be modified, provided that this does not alter its basic principle.

The invention claimed is:

1. A system for controlling one or more functions of one or more medical devices, the system comprising:
   an operator tracking unit arranged to determine a silhouette of a body part, hand, facial feature, or entire body of the operator;
   an evaluation device arranged to evaluate the determined silhouette;
   a control device arranged to control the function of the medical device; and
   an operating mode selector and a pedal or switch, wherein the operating mode selector selects between four or more operating modes, the first operating mode being one of maximum safety which requires pressing of the pedal or switch in combination with silhouette detection, a second operating mode which is fully automatic and requires only silhouette detection, a third operating mode which requires only pressing of the pedal or switch, and a fourth operating mode which requires silhouette detection to activate the function of the medical device and the function continues until it is deactivated by pressing of the pedal or switch or by another silhouette detection.

2. The system of claim 1, wherein the silhouette is of a gaze direction of the head of the operator.

3. The system of claim 1, further comprising a video camera detector for detecting the silhouette.

4. The system of claim 1, wherein the evaluation device is a computer programmed to receive the determined silhouette and evaluate the gesture of the silhouette.

5. The system of claim 1, wherein the controlling of the function of the medical device is that the control device automatically activates or deactivates a radiation source of the medical device based on the evaluation of the determined silhouette.

6. The system of claim 1, further comprising that the controlling of the function of the medical device is done in combination with voice command.

7. The system of claim 1, wherein the control device controls other devices in synchronization with the function of the medical device.

8. The system of claim 1, wherein the control device includes an adjustable timer to delay the deactivation of the function of the medical device.

9. The system of claim 1, wherein the medical device is a diagnostic or therapeutic device.

10. A method for controlling one or more functions of one or more medical devices, the method comprising:
    determining a silhouette of a body part, hand, facial feature, or entire body of an operator;
    evaluating the determined silhouette;
    controlling the function of the medical device based on the determined silhouette; and
    operating a mode selector and a pedal or switch, wherein the mode selector selects between four or more operating modes, the first operating mode being one of maximum safety which requires pressing of the pedal or switch in combination with silhouette detection, a second operating mode which is fully automatic and requires only silhouette detection, a third operating mode which requires only pressing of the pedal or switch, and a fourth operating mode which requires silhouette detection to activate the function of the medical device and the function continues until it is deactivated by pressing of the pedal or switch or by another silhouette detection.

11. The method of claim 10, wherein the silhouette is of a gaze direction of the head of the operator.

12. The method of claim 10, further comprising determining the silhouette of an operator with a video camera.

13. The method of claim 10, wherein the evaluating the determined silhouette is performed with a computer programmed to receive the determined silhouette and evaluate the gesture of the silhouette.

14. The method of claim 10, wherein the controlling of the function of the medical device is that the control device automatically activates or deactivates a radiation source of the medical device based on the evaluation of the determined silhouette.

15. The method of claim 10, wherein the medical device is a diagnostic or therapeutic device.

* * * * *